(12) United States Patent
Kuo

(10) Patent No.: US 7,914,283 B2
(45) Date of Patent: Mar. 29, 2011

(54) ACTIVATABLE DENTAL APPLIANCE

(75) Inventor: Eric Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 140 days.

(21) Appl. No.: 11/999,984

(22) Filed: Dec. 6, 2007

(65) Prior Publication Data
US 2009/0148803 A1 Jun. 11, 2009

(51) Int. Cl.
*A61C 3/00* (2006.01)
(52) U.S. Cl. .................................. 433/18; 433/6; 433/24
(58) Field of Classification Search ................ 433/6, 24, 433/18
See application file for complete search history.

(56) References Cited

U.S. PATENT DOCUMENTS

| 6,814,574 | B2 | 11/2004 | Abolfathi et al. |
| 7,374,421 | B2* | 5/2008 | Solomon .......................... 433/18 |
| 2005/0048433 | A1* | 3/2005 | Hilliard ............................ 433/24 |
| 2006/0188834 | A1* | 8/2006 | Hilliard ............................ 433/24 |
| 2008/0254402 | A1* | 10/2008 | Hilliard ............................ 433/24 |

* cited by examiner

*Primary Examiner* — Cris L Rodriguez
*Assistant Examiner* — Eric Rosen
(74) *Attorney, Agent, or Firm* — Kilpatrick Townsend and Stockton LLP

(57) ABSTRACT

An activatable dental appliance. A concave trough conforms to a plurality of teeth when placed over the plurality of teeth. A first force applying region is configured to apply a first force to at least one tooth of the plurality of teeth for repositioning the tooth. A second force applying region is configured to be selectively activated, wherein when selectively activated the second force applying region applies a force to at least one tooth of the plurality of teeth.

21 Claims, 11 Drawing Sheets

ACTIVATABLE DENTAL APPLIANCE

FIELD

Embodiments of the present invention relate in general to the field of orthodontics.

BACKGROUND

Orthodontic treatments involve repositioning misaligned teeth and improving bite configurations for improved cosmetic appearance and dental function. Repositioning is often accomplished by applying light continuous forces to a patient's teeth over an extended period of time. As part of the process of moving from the initial dental configuration to the final desired end configuration, the teeth typically undergo a transition through a series of intermediate configurations.

Conventionally, repositioning of teeth has been accomplished by what are commonly referred to as "braces." Braces comprise a variety of appliance components such as brackets, bands, archwires, ligatures, and O-rings. After the brackets and bands are affixed or bonded to the teeth, periodic meetings with the orthodontist are required so that the orthodontist can reactively adjust the archwires to create a new directional forces that continue to move the teeth closer to the desired position. This may involve installing different archwires having different force-inducing properties, adjusting the shape of the archwires, and/or replacing or tightening the ligatures that secure the wire to the fixed appliance.

An alternative to braces includes the use of aligner-type dental appliances for realigning teeth. Such an appliance may be comprised of a thin shell of material that forms a receiving cavity geometry that generally conforms to a patient's teeth but is slightly out of alignment with the initial tooth configuration. Placement of the dental appliances over the teeth applies controlled forces in specific locations to gradually move the teeth into a new predetermined configuration. Repetition of this process with successive appliances comprising new configurations eventually moves the teeth through a series of predetermined intermediate arrangements along the most effective and efficient treatment path to a final predetermined arrangement.

Aligner-type dental appliances may only be effective over a certain period of time due to the limited effective range of the active components of the appliance. After a certain time, the usefulness of the dental appliance is reduced by moving the teeth to the desired location, by a loss in resiliency in the dental appliance, or a combination of the two. Once the usefulness of the aligner dental appliance is reduced, the dental appliance is typically disposed of, and the next dental appliance in the treatment series is used. Hence, the shorter the useful lifespan of the dental appliance, the more frequently the dental appliance needs to be changed or adjusted. Consequently, a reduction in the lifespan of the dental appliance can require a greater number of dental appliances to achieve a desired dental result.

SUMMARY

An activatable dental appliance is described herein. In one embodiment, the activatable dental appliance comprises a concave trough that conforms to a plurality of teeth when placed over the plurality of teeth. A first force applying region is configured to apply a first force to at least one tooth of the plurality of teeth for repositioning the tooth. A second force applying region is configured to be selectively activated, wherein when selectively activated the second force applying region applies a force to at least one tooth of the plurality of teeth.

DESCRIPTION OF EMBODIMENTS

In the following description, numerous specific details are set forth in order to provide a thorough understanding. However, it will be recognized by one of ordinary skill in the art that embodiments may be practiced without these specific details. In other instances, well known methods, procedures, and components have not been described in detail as not to unnecessarily obscure aspects of the present invention.

Overview

Embodiments in accordance with the present invention extend the useful lifespan of the dental appliance by including additional activatable force regions that can be activated after the initial forces have been depleted.

Specifically, various embodiments disclose an activatable dental appliance. The activatable dental appliance comprises a concave trough which conforms to a plurality of teeth when placed over the plurality of teeth. In other words, upon placement, controlled forces are applied to the teeth as the appliance conforms in specific locations to gradually move the teeth into a new predetermined configuration. A first force applying region (e.g., a specific location), is configured to apply a first force to at least one tooth for repositioning the tooth. The first force is applied by the dental appliance in a standard manner. However, in one embodiment, once the useful lifespan of the dental appliance is sufficiently exhausted, a second force applying region(s) is/are selectively activated. When selectively activated the second force applying region(s) applies a force to at least one tooth of the plurality of teeth. Hence, a second force can be selectively activated in a dental appliance once the first force generated by the dental appliance is no longer useful. Accordingly, embodiments of the present invention provide an activatable dental appliance that extends the life and usefulness of the dental appliance.

System and Method for Positioning Teeth

As is known in the art, in order to fabricate an incremental position adjustment dental appliance, an initial digital data set (IDDS) representing an initial tooth arrangement and a final digital data set (FDDS) representing a final tooth arrangement are generated. Based on both the IDDS and the FDDS, a plurality of intermediate digital data sets (INTDDSs) are defined to correspond to incrementally adjusted dental appliances. The INTDDSs are defined using techniques for aligning teeth that can mimic how the teeth might move if treated with fixed orthodontic appliances. Thereafter, a set of incremental position adjustment dental appliances are produced based on the INTDDs and the FDDS. The dental appliances are designed to be worn over the teeth and to reposition the teeth to each of the tooth arrangements.

Figure 1:
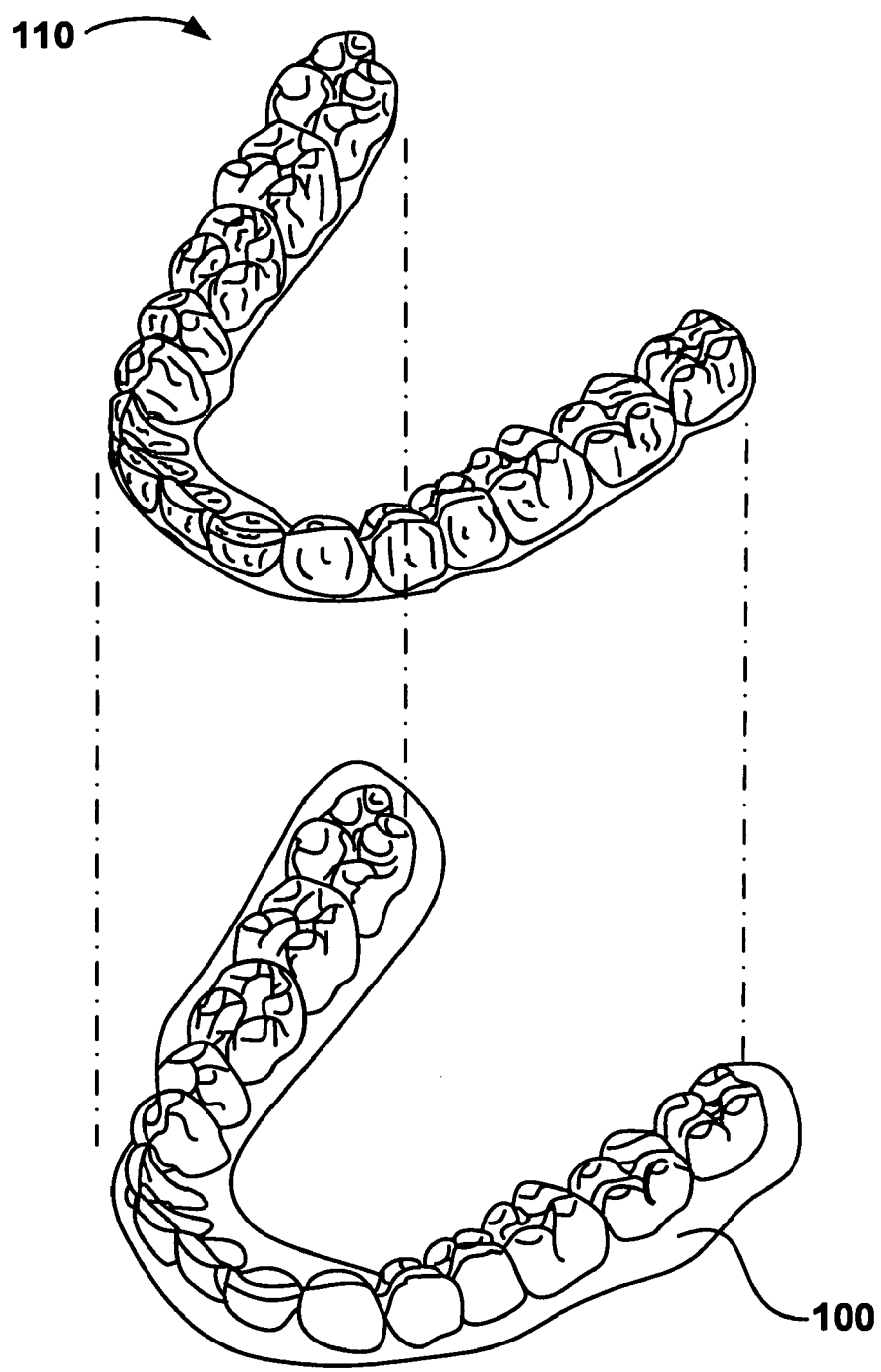
FIG. 1 illustrates a jaw with an incremental position adjustment dental appliance upon which embodiments of the present invention may be implemented.

Referring now to FIG. 1, a single adjustment dental appliance 110 which is worn by the patient in order to achieve an incremental repositioning of a lower jaw 100 is shown. The dental appliance 110 is one of a series of incremental position adjustment dental appliances worn by the patient to realign teeth from an initial arrangement to a final arrangement.

The example dental appliance 10 comprises a polymeric shell having a cavity shaped to receive and resiliently reposition teeth from one tooth arrangement to a successive tooth arrangement. In one embodiment, the polymeric shell will fit over all teeth present in the upper or lower jaw. On occasion, only certain one(s) of the teeth will be repositioned while others of the teeth will provide a base or anchor region for holding the dental appliance in place as it applies the resilient repositioning force against the tooth or teeth to be repositioned. Certain areas of the appliance will confer orthodontic forces on the teeth due to the intentional mismatch built into the appliance between the tooth's current position and the desired position built into the appliance. These are the inherently "active" regions of the appliance. Certain areas of the appliance will conform to the teeth nearly exactly as they are, without introducing orthodontic forces onto the teeth to which they conform. These are the inherently "passive" areas of the appliance which retain the teeth as they are in their current state.

The planning and fabrication of such dental appliances as an example elastic polymeric positioning appliance is described in detail in U.S. Pat. No. 5,975,893, and in published PCT application WO 98/58596 which designates the United States and which is assigned to the assignee of the present application. Systems of dental appliances employing technology described in U.S. Pat. No. 5,975,893, are commercially available from Align Technology, Inc., Santa Clara, Calif., under the tradename, Invisalign System. Align Technology, Inc., is the assignee of the present application.

Activatable Dental Appliance

Throughout the body of the Description of Embodiments, the use of the terms "aligner" or "dental aligner" is synonymous with the use of the terms "appliance" and "dental appliance" in terms of dental applications. For purposes of clarity, embodiments are hereinafter described within the context of the use and application of dental appliances, and more specifically "dental appliances."

Figure 2A:
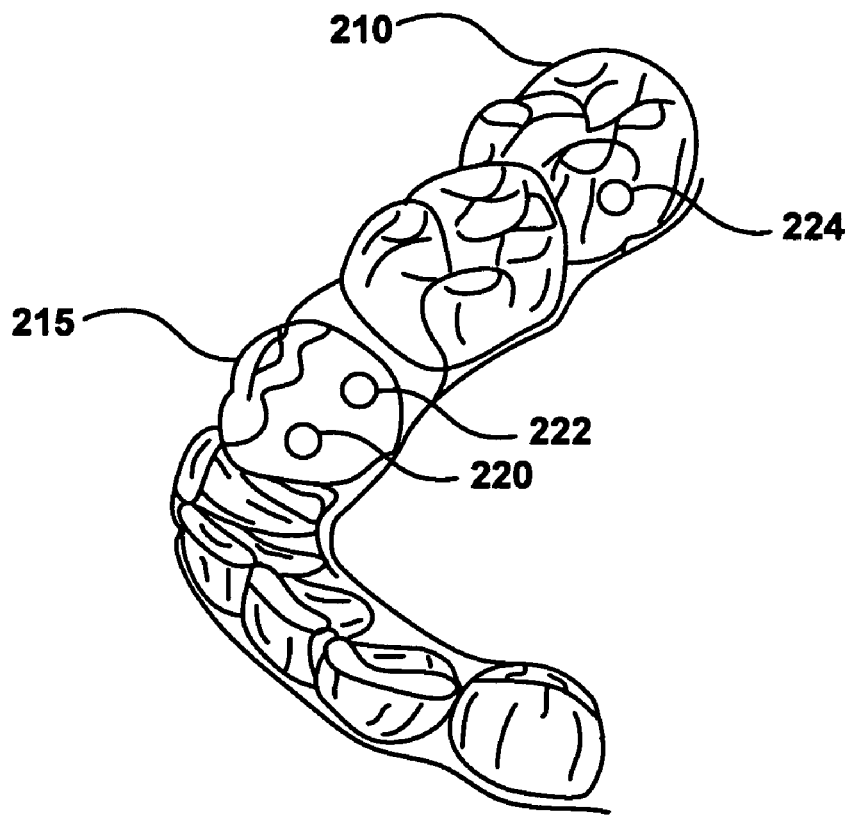
FIG. 2A illustrates an activatable dental appliance including an active region and a passive region, in accordance with one embodiment.

FIG. 2A illustrates an activatable dental appliance 210 including an active region 215 and a passive region 220, in accordance with one embodiment. Activatable dental appliance 210 includes a concave trough that generally conforms to a patient's teeth but is slightly out of alignment with an initial or immediately prior tooth configuration. The slight misalignment is caused by active region 215 and is for applying a predetermined force to a tooth in a predetermined direction for moving at least one tooth to a desired location. It should be appreciated that active region 215 and passive region 220 are established prior to formation of activatable dental appliance 210.

The "activatable" portion of the appliance is the area of the device that begins passive but becomes active as a result of user activation of the device. The appliance furthermore, is activatable, because of a relief portion built into the appliance that will accommodate the tooth movement once the appliance is activated. In one embodiment, an area of relief is built into the appliance in anticipation of the desired tooth movement. Furthermore, the area(s) on the appliance that can be adjustable are indicated such that the user can identify precisely the locations on the appliance where adjustments should be positioned.

Specifically, FIG. 2A shows activatable dental appliance 210 including passive regions 220, 222, 224, 226, 228 for the purpose of moving a tooth upon activation in the course of orthodontic treatment. Activatable dental appliance 210 is shaped to receive and resiliently reposition a patient's dentition. For example, the active region 215 may apply a first force to a tooth for purposes of repositioning the tooth.

Moreover, dental appliance 210 includes a space for providing an unobstructed path for avoiding interferences between the path of tooth and the appliance when repositioning a tooth. For example, dental appliance 200 may include a space on the opposite side of the tooth from passive region 220. Upon activation, force exerted by activating passive region 220 may reposition the tooth into the space. The absence of interference enables the tooth to move from its current position to the desired position once the appliance is activated. This is important because interference by the appliance can prevent a tooth from moving to the desired final position.

It should be appreciated that active region 215 may generate a force oriented in any direction depending on the direction of desired repositioning, such as and without limitation, rotation, translation, inclination, angulation, intrusion, and extrusion. That is, the generated force can be a translational or rotational force along any of the tooth's directional axes or any combination of these directions, in various embodiments.

Passive region 220, upon activation into an active region, may apply a second force to a tooth. Similarly, one of multiple passive regions 220-224 on a single tooth, upon activation into an active region, may generate one or more forces in any direction. For example, in one embodiment, by activating passive regions 220 and 222, simultaneously, the respective tooth would rotate and possibly extrude the tooth, depending on their relationship to each other and the tooth contour. In another embodiment, if regions 220 and 222 were activated simultaneously, the respective tooth would likely translate and possibly tip, depending on their relationship to each other and the tooth contour.

It should be appreciated that dental appliance 210 may include any number of active regions and passive regions. In addition, passive regions 220-224 can be activated in any order, and can exert forces concurrently or sequentially, depending on the needs of the orthodontic treatment. Furthermore, it should be appreciated that passive regions may overlap, such that two passive regions apply forces to the same location in sequential incremental repositionings (not shown). It is important to note that an appliance may be completely passive and only moves teeth upon activation of one or more regions. Or there may be active regions in conjunction with activatable regions within the same appliance. It should also be appreciated that in one embodiment active region 215 resides on a buccal side and a passive region (e.g., passive region 220) resides on a lingual side of the same tooth. Moreover, active region 215 may reside adjacent to the gingival and the passive region may reside adjacent to the cusp of the same tooth.

In one embodiment, activatable dental appliance 210 is designed digitally as a three-dimensional (3D) model prior to being manufactured. For example, activatable dental appliance 210 is based at least on a plurality of INTDDSs as described above. At least two sequential INTDDSs are digitally merged, where the first INTDDS is associated with forces generated by active region 215 and where the second INTDDS is associated with forces generated upon the activation of passive region 220. The 3D model can be tested prior to manufacture for digitally testing the forces exerted by active region 215 and passive region 220 upon activation. In addition to the merging of the sequential INTDDS, the union geometric path taken between one INTDDS and the subsequent INTDDS is defined such that the tooth to be moved can be done in such a way where the tooth is unobstructed by the appliance if moved from the current to the desired state. This allows the activation of the appliance to move the tooth in an unobstructed manner, free of interference between the tooth and the appliance in its intended path.

Figure 2B:
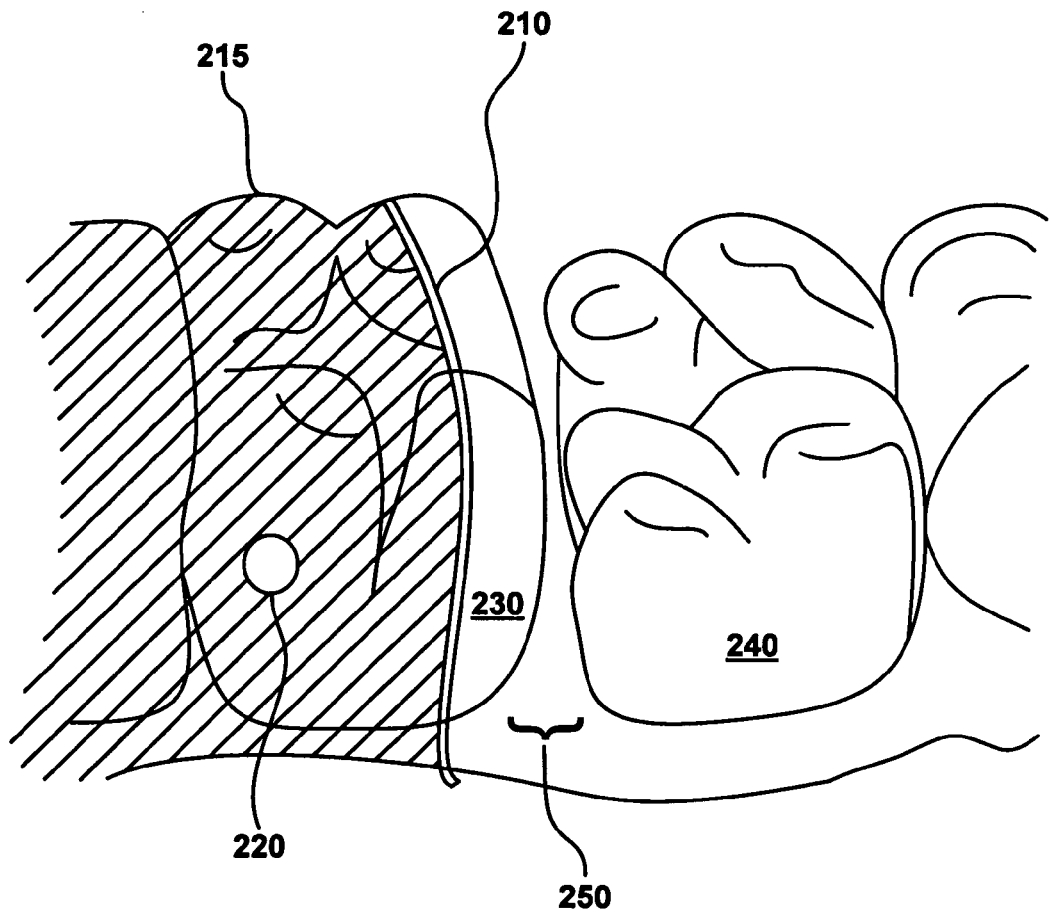
FIG. 2B illustrates interaction of an activatable dental appliance and a tooth, in accordance with one embodiment.

FIG. 2B illustrates interaction of an activatable dental appliance and a tooth, in accordance with one embodiment of the present invention. As shown in FIG. 2B, a partial representation of activatable dental appliance 210 is shown being worn over the patient's dentition. In particular, activatable dental appliance 210 is shown being worn over the tooth 230. In an initial configuration, active region 215 applies a force to tooth 230 for purposes of repositioning, and passive region 220 is not activated, and thus applies no force to tooth 230.

Active region 215 applies a repositioning force to tooth 230, for instance, to move tooth 230 closer to tooth 240 for reducing gap 250. As shown, active region 215 applies a force to tooth 230 in a combined translational force towards tooth 240 and a lingual direction force towards the tongue. As described above, active region 215 applies a force for incrementally repositioning a tooth, and only applies the force for a certain period of time. That is, the force stored within a dental appliance may only be effective for a given time period, e.g., one or two weeks.

Embodiments of the present invention provide for activating passive regions of activatable dental appliance 210, such that additional forces can be generated for repositioning a tooth, thereby extending the life and usefulness of dental appliance 210. For example, activating passive region 220 causes a second force to be applied to tooth 230 to move tooth 230 closer to tooth 240 for reducing gap 250. As shown, upon activation, region 220 applies a force for incrementally repositioning tooth 200 in a combined translational force towards 240 and a facial direction towards the side of the mouth.

It should be appreciated that a passive region such as passive region 220 can be activated in many different ways. For instance, and without limitation, passive region 220 may be activated using an activation tool, such as pliers. It may be necessary to heat the activation tool to allow activatable dental appliance 210 to deform for activation of passive region 220. In another embodiment, passive region 220 may be activated by a finger applying pressure to the passive region to create a force applying bump.

Figure 2C:
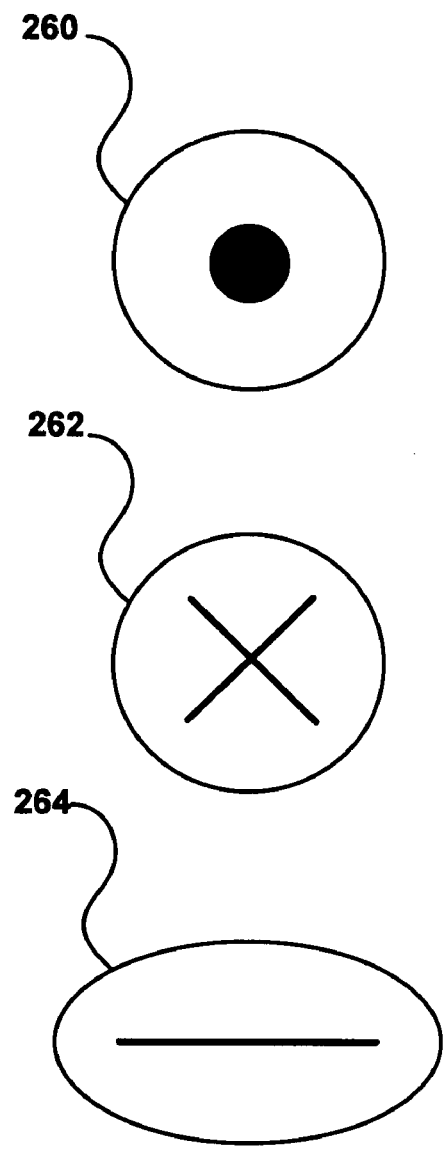
FIG. 2C illustrates example indications for indicating a location of a passive region of an activatable dental appliance, in accordance with embodiments.

In various embodiments, in order to ensure that passive region 220 is properly activated, activatable dental appliance 210 includes an indication for indicating a location of passive region 220. FIG. 2C illustrates example indications. For example, indication 260 includes an outer circle and an inner circle, and indication 262 includes an outer circle and an "X". It should be appreciated that passive regions need not be circular, but rather can be any shape. Indication 264 illustrates an elliptical shaped passive region, and includes a straight line. Indications 260, 262 and 264 may be printed or placed on dental appliance 210. It should be appreciated that indications 260, 262 and 264 are examples, and that activatable dental appliance 210 can include an indication of all different shapes and sizes.

It should be appreciated that the indication may also indicate how to deform activatable dental appliance 210 for properly activating passive region 220. For example, with reference to indication 260, dental appliance 210 may be deformed such that the inner circle is depressed until deformation extends to the outer circle. Similarly, with reference to indication 264, the line may be depressed until deformation extends to the outer ellipse.

Figure 4A:
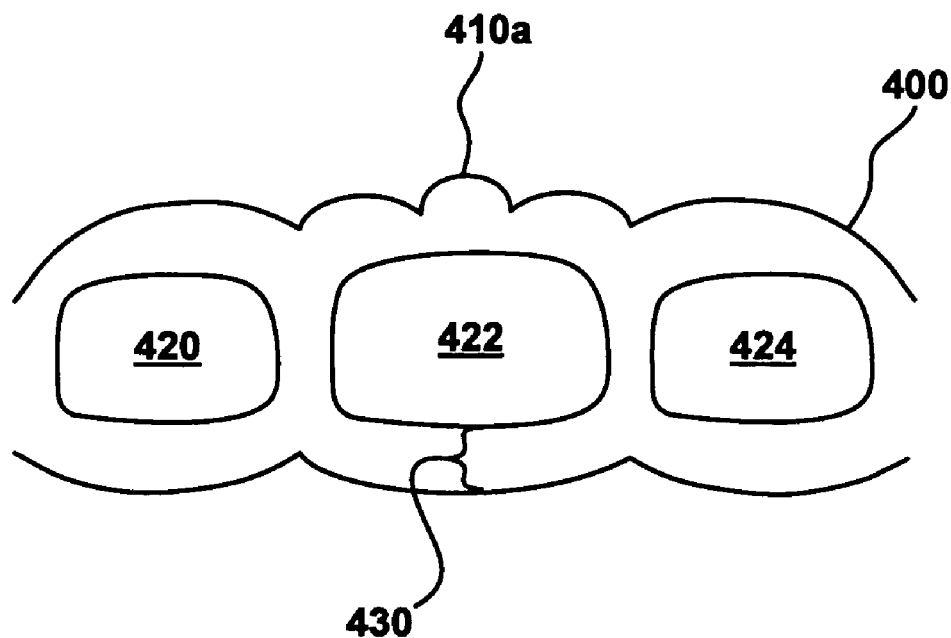
FIG. 4A illustrates a top-down cut-away view of interaction between a tooth and an activatable dental appliance including a passive region prior to activation, in accordance with an embodiment.
Figure 4B:
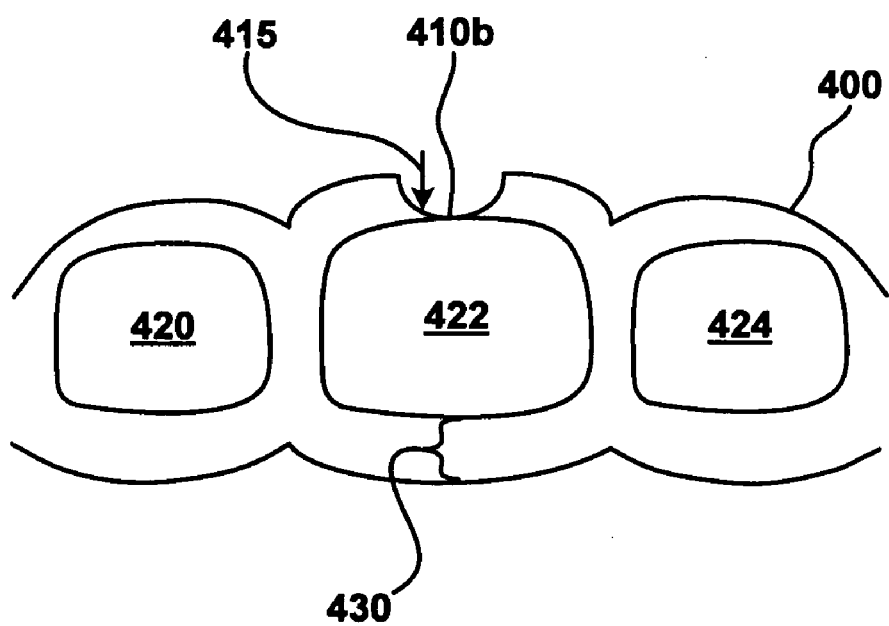
FIG. 4B illustrates a top-down cut-away view of interaction between a tooth and an activatable dental appliance including an activated passive region, in accordance with an embodiment.

In other embodiments, the indication is a bump 310a on the outer surface of the dental appliance 300 that is activated to become a bump on the inner surface of the dental appliance. FIGS. 4A and 4B illustrate the activation of a passive bump on the outer surface of an activatable dental appliance.

Figure 3A:
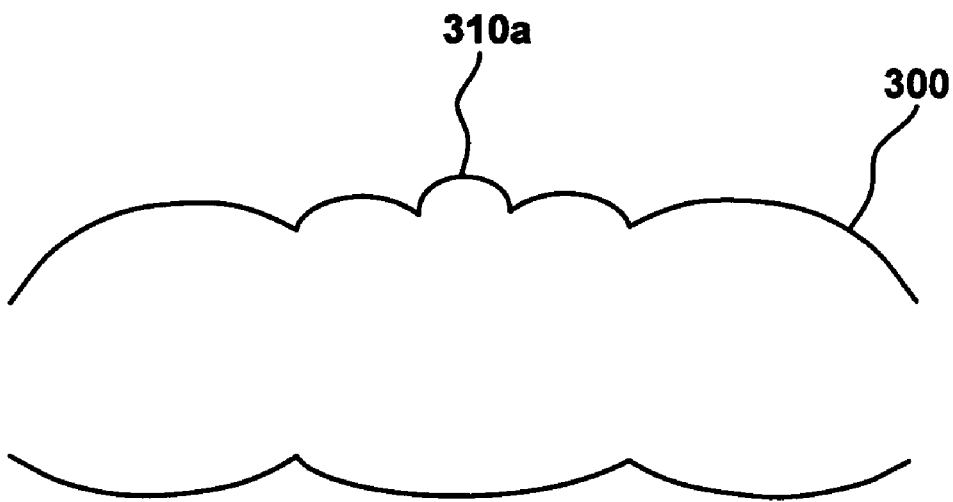
FIG. 3A illustrates a top-down cut-away view of an activatable dental tray including a passive region prior to activation, in accordance with an embodiment.

As shown in the embodiment of FIG. 3A, activatable dental appliance 300 includes passive bump 310a. In an initial state, passive bump 310a extends out from the outer surface of dental appliance 300. It should be appreciated that passive bump 310a is established prior to formation of activatable dental appliance 300. Passive bump 310a is activated by pressing bump 310a into dental appliance 300. Although passive bump 310a is shown on the buccal side of a tooth, it may be located on the lingual side as well (see FIG. 2A).

Figure 3B:
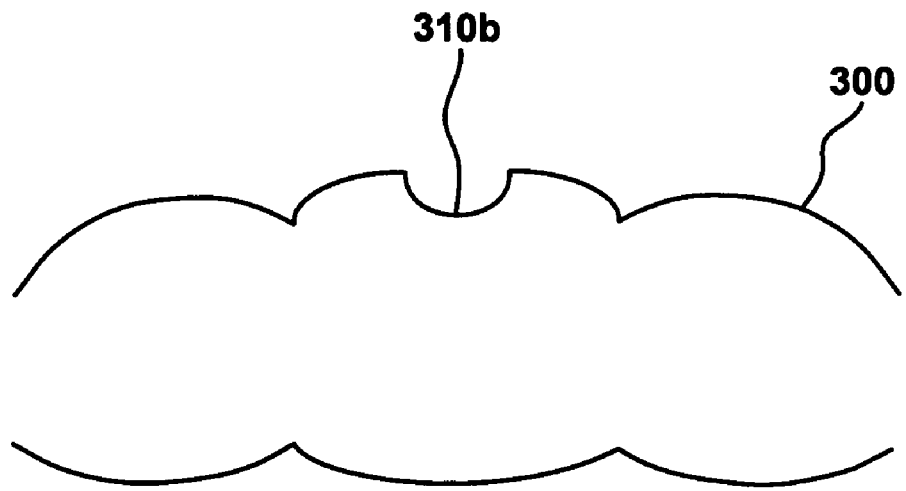
FIG. 3B illustrates a top-down cut-away view of an activatable dental appliance including an activated passive region, in accordance with an embodiment.

As shown in FIG. 3B, upon activation, active bump 310b extends into dental appliance 300. In an activated state, upon placing dental appliance 300 over the patient's dentition, active bump 310b applies a force to a tooth. It should be appreciated that bump 310b may be of such a shape to apply a specific force. For instance, a larger bump may provide a larger force on a tooth, depending on the location and orientation of the bump.

While the indication is described in detail herein as being printed on the dental appliance or a bump formed within the dental appliance, it should be appreciated that others forms of indicia may be used. For example, an indentation or series of indentations may be formed or stamped into the activatable dental appliance for indicating the location of the passive region.

Figure 4C:
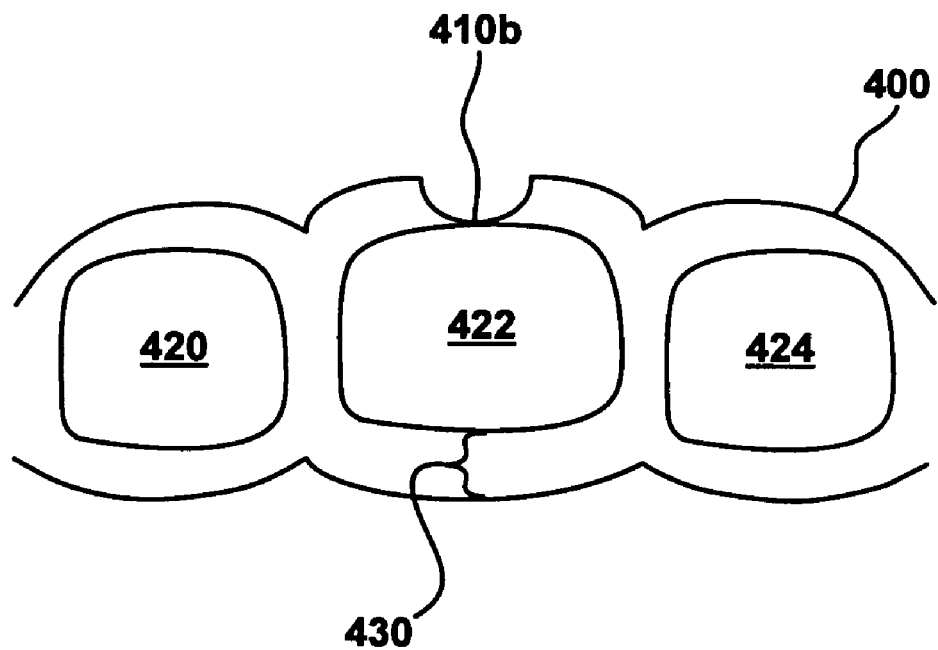
FIG. 4C illustrates a top-down cut-away view of interaction between a tooth and an activatable dental appliance including an activated passive region after tooth movement, in accordance with an embodiment.

FIGS. 4A-C illustrate the interactions of an activatable dental appliance on a tooth. Specifically, FIGS. 4A-C illustrate the movement of a tooth through the use of forces generated by activating a passive bump on the outer surface of the dental appliance in the course of orthodontic treatment.

As shown in FIG. 4A, activatable dental appliance 400 includes passive bump 410a. Dental appliance 400 generally conforms to teeth 420, 422 and 424 of a patient's dentition. In an initial state, passive bump 410a extends out from the buccal or outer surface of dental appliance 400. It should be appreciated that passive bump 410a is established prior to formation of activatable dental appliance 400. Passive bump 410a is activated by pressing bump 410a into dental appliance 400. Moreover, dental appliance 400 includes space 430 for providing an unobstructed path for avoiding interferences in repositioning tooth 422. As shown, space 430 is on the opposite or lingual side of tooth 422 as bump 410a.

As shown in FIG. 4B, upon activation, active bump 410b extends into dental appliance 400. In an activated state, active bump 410b applies a force to tooth 422, where the direction of force is indicated by arrow 415. It should be appreciated that bump 410b may be of such a shape to apply a specific force. For instance, a larger bump may provide a larger force on a tooth, depending on the location and orientation of the bump. The force as indicated by arrow 415 repositions tooth 422, directing tooth 422 into space 430. As mentioned earlier, an alternative embodiment may include the bump 410b having still another bump that would surround bump 410b, so that when activated would further extend bump 410b against the tooth 422 to create a new force at the same or near same location as bump 410a.

FIG. 4C illustrates dental appliance 400 where active bump 410b has moved tooth 422 such that bump 410b no longer applies any force to tooth 422. Accordingly, space 430 has been reduced, as tooth 422 has moved into space 430.

Figure 5:
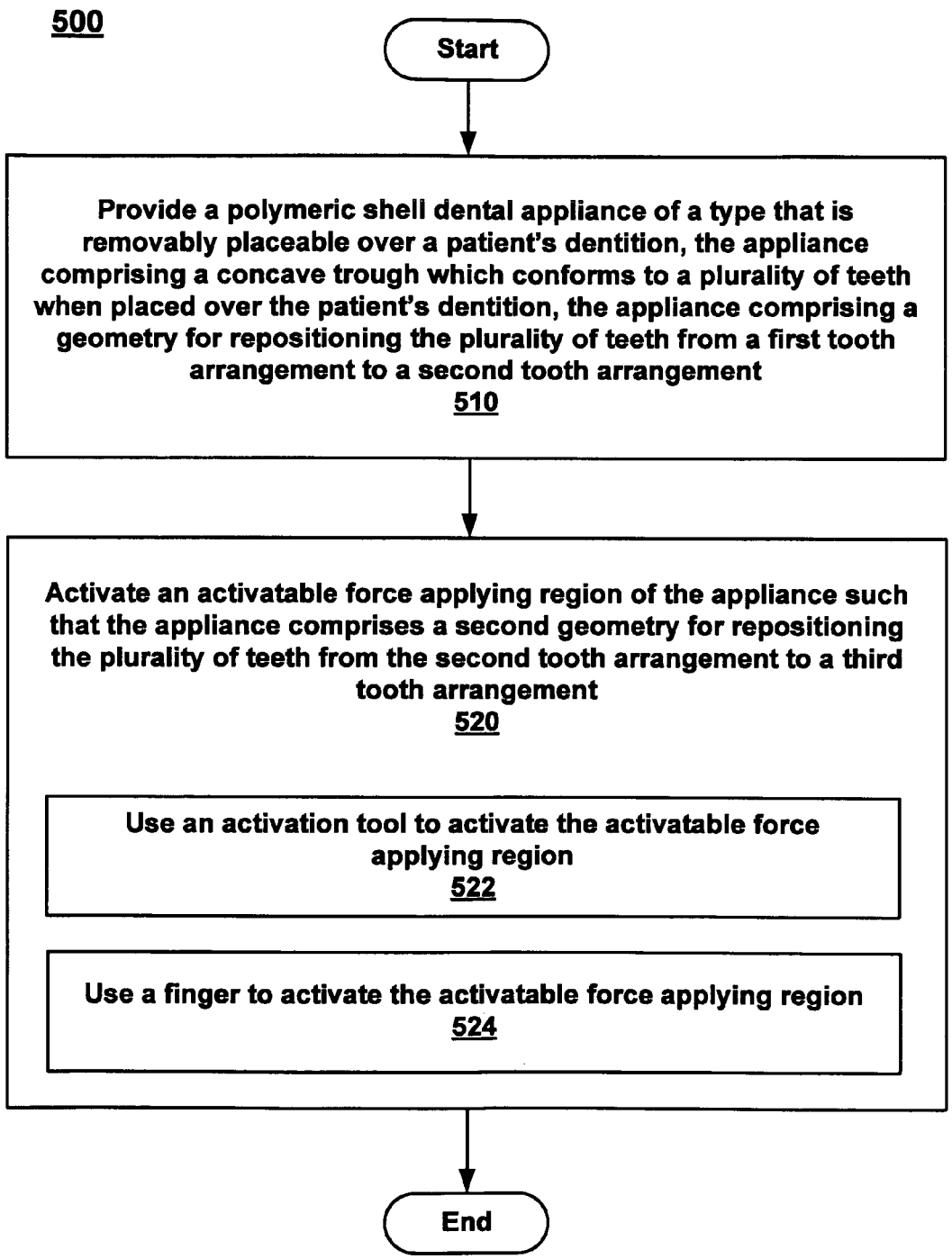
FIG. 5 is a flow chart of a method for repositioning teeth, in accordance with one embodiment.

FIG. 5 is a flow chart of a method 500 for repositioning teeth, in accordance with one embodiment of the present invention. The present embodiment provides an activatable dental appliance including activatable force applying regions. As such, embodiments of the present invention are capable of providing multiple stage incremental repositioning of teeth.

At step 510, the present embodiment provides a polymeric shell dental appliance of a type that is removably placeable over a patient's dentition. The appliance includes a concave trough which conforms to a plurality of teeth when placed over the patient's dentition, and includes a geometry for repositioning the plurality of teeth from a first tooth arrangement to a second tooth arrangement. For illustration, FIGS. 3A and 3B show an activatable dental appliance 210. Active region 215 at least in part defines the geometry for repositioning tooth 230.

Subsequently, as shown at step 520, an activatable force applying region of the appliance is activated such that the appliance includes a second geometry for repositioning the plurality of teeth from the second tooth arrangement to a third tooth arrangement. For illustration, with reference to FIG. 2B, passive region 220 at least in part defines the second geometry for further repositioning tooth 230.

Figure 6:
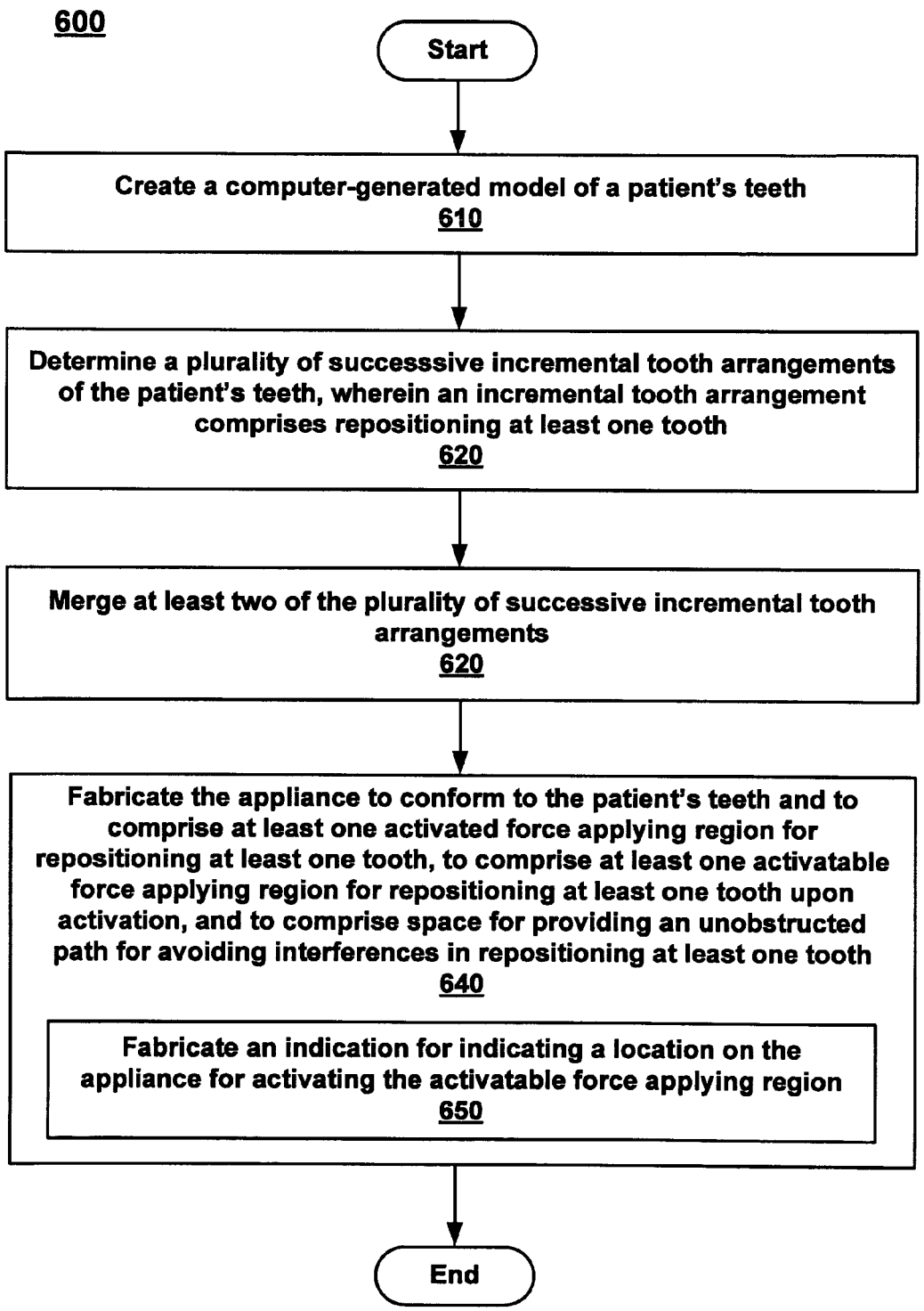
FIG. 6 is a flow chart of a method for fabricating a dental appliance for repositioning at least one tooth, in accordance with one embodiment.

In one embodiment, as shown at step 522, an activation tool is used to activate the activatable force applying region. In another embodiment, as shown at step 524, a finger is used to activate the activatable force applying region FIG. 6 is a flow chart of a method 600 for fabricating a dental appliance for repositioning at least one tooth, in accordance with one embodiment of the present invention. The present embodiment provides an activatable dental appliance including activatable force applying regions. As such, embodiments are capable of providing multiple stage incremental repositioning of teeth.

At step 610, a computer-generated model of a patient's teeth is created. For illustration, a 3D computer model of jaw 100 of FIG. 1 is generated. A computer simulation is capable of modeling interactions among the teeth on jaw 100. The 3D model can be used to simulate jaw movements including protrusive motions, lateral motions, and "tooth guided" motions where the path of lower jaw 100 is guided by teeth contacts rather than by anatomical limits of jaw 100. Motions are applied to one jaw, but may also be applied to both the lower and upper jaws. Based on the computer-generated model, the final arrangement of the teeth in jaw 100 can be ascertained.

At step 620, a plurality of successive incremental tooth arrangements of the patient's teeth are determined, wherein an incremental tooth arrangement comprises repositioning at least one tooth. As described above, a plurality of INTDDSs are defined to correspond to incrementally adjusted dental appliances. The INTDDSs are defined using techniques for aligning teeth, which in general, mimic the way that teeth move when fixed orthodontic brackets and wires are used. However, unlike the reactive process of conventional bracket and wire orthodontics, predetermined INTDDSs are defined to provide a specific force along the most effective treatment path.

At step 630, at least two of the successive incremental tooth arrangements are merged and the union of the path from one arrangement to the successive arrangement determined. The merging of two successive incremental tooth arrangements allows for determining active force applying regions and activatable force applying regions for each tooth. For illustration, FIG. 2A shows activatable digital appliance 210 based at least on a plurality of INTDDSs as described above. At least two sequential INTDDSs are digitally merged, where the first INTDDS is associated with forces generated by active region 215 and where the second INTDDS is associated with forces generated upon the activation of passive region 220. The 3D model can be tested for digitally testing the forces exerted by active region 215 and passive region 220 upon activation. For example, forces exerted by active region 215 and passive region 220 upon activation are applied to the 3D model for testing the movement of the teeth to a new position.

At step 650, an indication for indicating a location on the appliance for activating the activatable force applying region is created. Thereafter, an appliance is fabricated. The appliance conforms to the patient's teeth and includes at least one activated force applying region for repositioning at least one tooth, includes at least one activatable force applying region for repositioning at least one tooth upon activation, and includes space for providing an unobstructed path for avoiding interferences in repositioning at least one tooth.

While the embodiments illustrated in methods 500 and 600 show specific sequences and quantity of steps, the present invention is suitable to alternative embodiments. For example, not all the steps provided for in the methods are required for the present invention. Furthermore, additional steps can be added to the steps presented in the present embodiment. Likewise, the sequences of steps can be modified depending upon the application.

Embodiments of the present invention, an activatable dental appliance, have been described herein. While the invention is described in conjunction with various embodiments, it is understood that they are not intended to limit the invention to these embodiments. On the contrary, the invention is intended to cover alternatives, modifications and equivalents, which may be included within the spirit and scope of the invention as defined by the appended claims.

What is claimed:

1. An activatable dental appliance, comprising:
    a shell having teeth receiving cavities shaped to receive and apply a resilient force to a patient's teeth, at least one tooth receiving cavity of the shell comprising:
        a bump formed at a predetermined location in the cavity and configured to deliver one or more forces to a tooth received in the at least one cavity, the bump being in a non-activated first state where the bump extends outward and away from the at least one cavity, and the bump further configured for inversion into an activated second state where the bump extends inward toward the at least one cavity so as to contact a received tooth, wherein the shape of the bump in the activated state is substantially the same as the shape of the bump in the non-activated state.

2. The dental appliance of claim 1, wherein the bump is configured to apply a predetermined force to a tooth received in the at least one cavity when activated.

3. The dental appliance of claim 2, wherein the bump has a size, shape and location selected to apply a predetermined force.

4. The dental appliance of claim 2, wherein the bump provides a radial length that is substantially the same in the activated state and non-activated state.

5. The dental appliance of claim 2, wherein the bump has a concave shape in the active and inactive state.

6. The dental appliance of claim 1, wherein the at least one cavity is configured to apply a first force when the bump is in the non-activated state and a second force when the bump is in the activated state.

7. The dental appliance of claim 1, the shell comprising a plurality of different force applying regions.

8. The dental appliance of claim 7, wherein the at least one cavity comprises a plurality of force applying regions.

9. The dental appliance of claim 7, comprising at least two force applying regions proximate to each other.

10. The dental appliance of claim 7, comprising at least two force applying regions disposed in the at least one cavity generally opposite each other.

11. The dental appliance of claim 1, wherein fabricating the appliance comprises designing digitally a 3D model before manufacturing a physical appliance.

12. The dental appliance of claim 1, wherein the bump is operable for activation by an activation tool.

13. The dental appliance of claim 1, wherein the bump is operable for activation by a user's finger.

14. The dental appliance of claim 1, wherein the bump is operable for activation by distorting a portion of the appliance proximate the bump or at least one cavity.

15. The dental appliance of claim 1, wherein the at least one cavity is configured to elicit a rotation, translate, tilt, impound, or extract movement.

16. The dental appliance of claim 1, the at least one cavity comprising a first force applying region residing on a buccal side of the at least one cavity and a second force applying region residing on a lingual side of the at least one cavity.

17. The dental appliance of claim 1, the at least one cavity comprising a first force applying region residing adjacent to a gingiva region of the cavity and a second force applying region resides adjacent to a cusp region of the cavity.

18. The dental appliance of claim 1, further comprising a relief portion space for accommodating tooth movement in response to contact force applied to a tooth received by the at least one cavity.

19. The dental appliance of claim 1, wherein the relief portion is on a side of the at least one cavity opposite to a side of the cavity having the bump.

20. An activatable dental appliance, comprising:
a shell defining a trough shaped to fit over and span a plurality of teeth of a patient's dental arch, the trough comprising at least one activatable tooth receiving cavity shaped to receive and resiliently position a tooth of the dental arch, the at least one activatable cavity comprising:
a bump formed in shell material defining the at least one activatable cavity, the bump being in a non-activated state where the bump extends outward or away from the at least one activatable cavity, and the bump further configured for inversion into an activated state where the bump extends inward toward the at least one cavity such that the bump in the second state is brought into contact with a tooth received by the at least one activatable cavity, the bump transitionable between the first state and second state in response to an applied pressure and wherein the shape of the bump in the activated state is substantially the same as the shape of the bump in the non-activated state;
a relief portion space for providing an unobstructed path accommodating tooth movement in response to a force applied to the tooth received by the at least one activatable cavity.

21. A system for positioning the teeth of a patient, comprising:
a series of incremental position adjustment dental appliances that when worn successively by the patient incrementally reposition the patient's teeth from an initial arrangement toward a final arrangement, the series comprising:
an activatable dental appliance forming a shell having teeth receiving cavities shaped to receive and apply a resilient force to a patient's teeth, at least one tooth receiving cavity of the shell comprising a bump formed at a predetermined location in the cavity, the bump being in a non-activated state where the bump extends outward and away from the at least one cavity, and the bump further configured for inversion into an activated state where the bump extends inward toward the at least one cavity so as to modify a tooth movement force applied to a received tooth, wherein the shape of the bump in the activated state is substantially the same as the shape of the bump in the non-activated state in response to a user-applied pressure;
wherein the activatable dental appliance with the bump in the non-activated state and the activatable appliance with the bump in the activated state represent planned successive appliances in the series.

* * * * *